US005366482A

United States Patent [19]

Brazeau

[11] Patent Number: 5,366,482

[45] Date of Patent: Nov. 22, 1994

[54] MOBILE TRACTION BED

[76] Inventor: David H. Brazeau, 9 Andrew Court, Newcastle, Ontario, L1B 1J5, Canada

[21] Appl. No.: 24,075

[22] Filed: Mar. 1, 1993

[51] Int. Cl.[5] .......................... A61F 5/00; A47C 21/08

[52] U.S. Cl. .................................... 606/244; 606/242; 5/428; 5/610

[58] Field of Search ........................ 606/241, 242, 244; 602/32, 33, 38, 39; 5/100, 408, 610, 611

[56] References Cited

U.S. PATENT DOCUMENTS

| | | | |
|---|---|---|---|
| 2,955,298 | 10/1960 | Rurka | 5/428 X |
| 3,741,200 | 6/1973 | Morin | 606/244 |
| 3,929,078 | 3/1976 | Smith et al. | 5/428 |
| 4,002,165 | 1/1977 | Lind | 606/242 X |
| 4,271,830 | 6/1981 | Moon | 606/244 |
| 4,535,762 | 8/1985 | Natchev | 606/244 |
| 4,621,625 | 11/1986 | Powlan | 602/33 |

*Primary Examiner*—Richard J. Apley
*Assistant Examiner*—Linda C. M. Dvorak

[57] ABSTRACT

A traction bed which can be moved from one location to another without harm or discomfort to the patient has a device for raising the bed to an angle such that the part of the body to be held in traction can be kept above the heart's level. The mobile traction bed also has a unique opening and closing side rail for keeping the patient safe and secure within the bed. The traction side of the bed can have a bar and sleeve for supporting traction weights. By using the mobile traction bed, the patient can rest at home instead of at the hospital, yet can be moved to and from the hospital as is required.

1 Claim, 3 Drawing Sheets

MOBILE TRACTION BED

BACKGROUND OF THE INVENTION

1. Field of the Invention

The present invention relates generally to beds, and more particularly, to an angularly raisable traction bed especially adapted so that the bed can be moved from one location to another.

2. Description of the Prior Art

Beds used in hospitals for keeping a patient in traction are well known in the prior art. When a person breaks a bone or for any reason requires traction, a long and expensive hospital stay has, in the past, usually been necessary. Typical beds utilized for traction arc large structures which remain at the hospital. In the case of a broken bone or the like, after the bone has set, the patient is often still required to stay in the hospital in traction for a substantial amount of time.

What is needed is some type of bed which can be used to keep a patient in traction and yet which can be easily moved from one location to another, such as from the hospital to the patient's home (and back and forth as is needed) so that much of the patient's recuperation can be done in the comfort of their own home at a cost substantially less than a long hospital stay.

It is known to have beds having one end of which is lifted to a higher level than the other (see for example U.S. Pat. Nos.4,312,088 and 4,651,365).

It is also known to have adjustable bed side rails (see for example U.S. Pat. No. 3,823,428).

Thus, while the foregoing body of prior art indicates it to be well known to use beds in hospitals to keep a patient in traction and to raise one end of a bed to a higher level than the other, the provision of a simple and cost effective device allowing for mobility from one location to another and use in one's own home has not been contemplated. Nor does the prior art described above teach or suggest a mobile traction bed device which may be used by individuals to easily and comfortably move from a hospital to the patient's home, and back and forth as is required. The foregoing disadvantages are overcome by the unique mobile traction bed of the present invention as will be made apparent from the following description thereof. Other advantages of the present invention over the prior art also will be rendered evident.

SUMMARY OF THE INVENTION

To achieve the foregoing and other advantages, the present invention, briefly described, provides a traction bed which can be moved from one location to another without harm or discomfort to the patient having a device for raising the bed to an angle such that the part of the body to be held in traction can be kept above the heart's level. The mobile traction bed also has a unique opening and closing side rail for keeping the patient safe and secure within the bed. The traction side of the bed can have a bar and sleeve for supporting traction weights. By using the mobile traction bed, the patient can rest at home instead of at the hospital, yet can be moved to and from the hospital as is required.

The above brief description sets forth rather broadly the more important features of the present invention in order that the detailed description thereof that follows may be better understood, and in order that the present contributions to the art may be better appreciated. There are, of course, additional features of the invention that will be described hereinafter and will form the subject matter of the claims appended hereto.

In this respect, before explaining the preferred embodiments of the invention in detail, it is to be understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which this disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms of phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

It is therefore an object of the present invention to provide a new and improved mobile traction bed which has all of the advantages of the prior art and none of the disadvantages.

It is another object of the present invention to provide a new and improved mobile traction bed which may be easily and efficiently manufactured and marketed.

It is a further objective of the present invention to provide a new and improved mobile traction bed which is of durable and reliable construction.

An even further object of the present invention is to provide a new and improved mobile traction bed which is susceptile of a low cost of manufacture with regard to both materials and labor, and which accordingly is then susceptible of low prices of sale to the consuming public, thereby making such mobile traction bed available to the buying public.

Still yet a further object of the present invention is to provide a new and improved mobile traction bed which can be moved from one location to another without harm of discomfort to the patient in traction.

It is still a further object of the present invention to provide a new and improved mobile traction bed having a device for raising the traction side of the bed so that the level of the area of the body to be kept in traction can be kept at a level above the level of the heart of the patient.

Still a further object of the present invention is to provide a new and improved mobile traction bed including means for opening and closing quickly and easily a side rail of the bed, thus allowing the patient to enter the bed and then keeping the patient safe and secure within the confines of the bed.

Still even yet a further object of the present invention is to provide a new and improved mobile traction bed having a cross bar and a sleeve at the traction side of the bed for supporting traction weights.

It is even still a further object of the present invention to provide a new and improved mobile traction bed allowing a patient in traction to go home to recuperate in traction instead of requiring a long and expensive stay at the hospital.

Still even a further object of the present invention is to provide a new and improved mobile traction bed which can also include attaching means for holding such objects as a magnetic chalkboard, a coloring table, a cup holder, a bell holder and the like.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawings wherein.

DESCRIPTION OF THE PREFERRED EMBODIMENT

With reference now to the drawings, a new and improved mobile traction bed embodying the principles and concepts of the present invention will be described.

Figure 1:
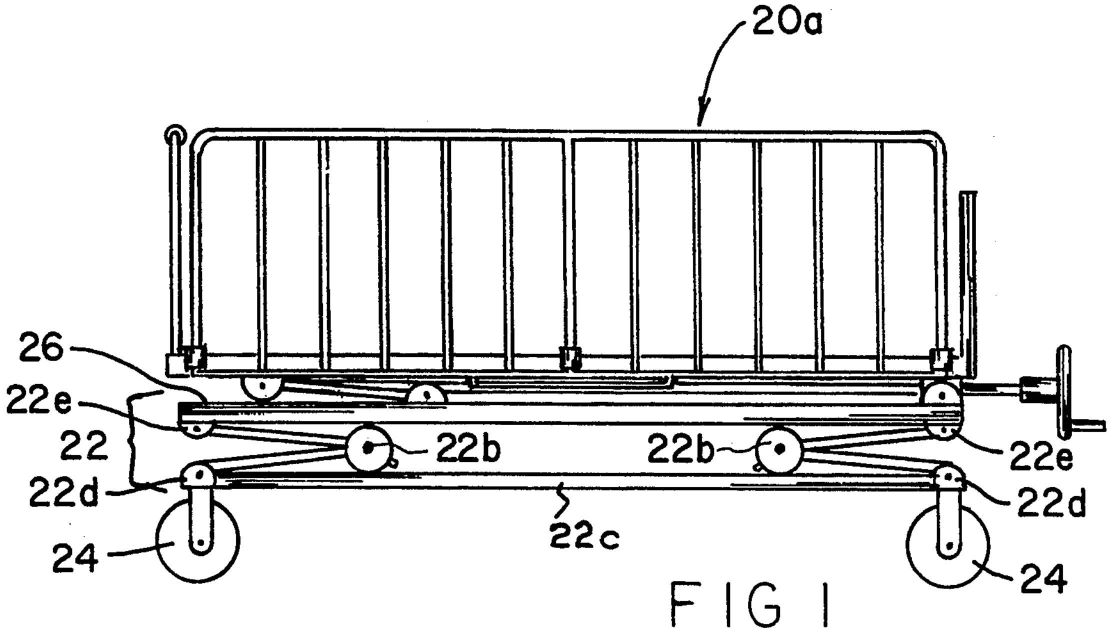
FIG. 1 is a side perspective view showing the preferred embodiment of the mobile traction bed in its level position in accordance with the present invention.
Figure 2:
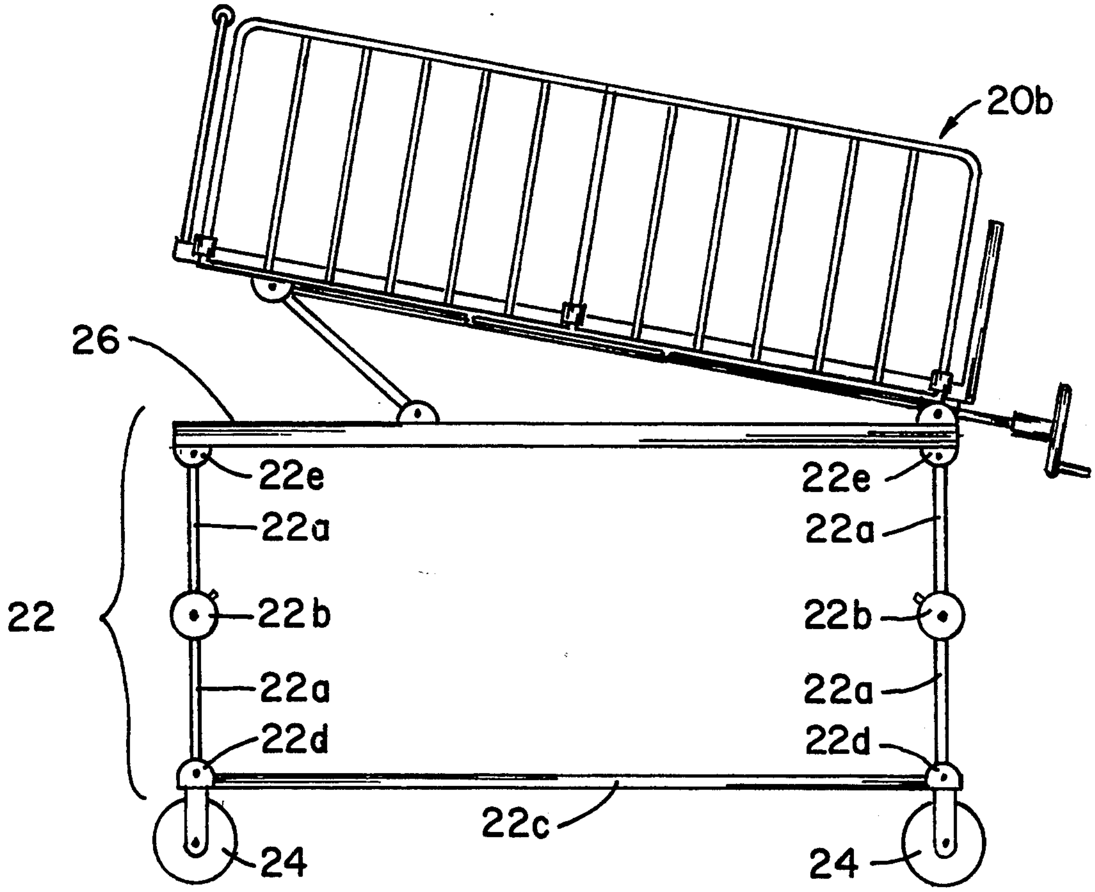
FIG. 2 is a side perspective view of the mobile traction bed of FIG. 1 in an elevated position in accordance with the present invention.

Turning initially to FIGS. 1–2, there is shown a first exemplary embodiment of the mobile traction bed of the invention generally designated by reference numeral 20*a* (see FIG. 1)in its storage position and reference numeral 20*b* (see FIG. 2) in its traction use position. In its preferred form, mobile traction bed 20*a* and 20*b* is generally comprised of a support structure 22 such as a modified gurney such as that used for stretchers. The support structure 22 has wheels 24 necessary to the invention to provide the mobility aspect. The actual construction of the support structure 22 is not a key feature of the present invention and any prior art type wheeled support structure will work with the present invention. In the support structure 22 shown in FIGS. 1 and 2, horizontal support bar 22*c* runs between the wheel supports 22*d*. Other horizontal support bars 22*c* not shown by the side views of the FIGS. 1 and 2 will run between the other wheel supports 22*d*. Vertical support bars 22*a* run between top support joints 22*e* central flex joints 22*b* and wheel supports 22*d*. The support structure 22 can be set in the storage position of FIG. 1 or in the use position of FIG. 2 with the support bars 22*a* fully extended as shown.

Figure 3:
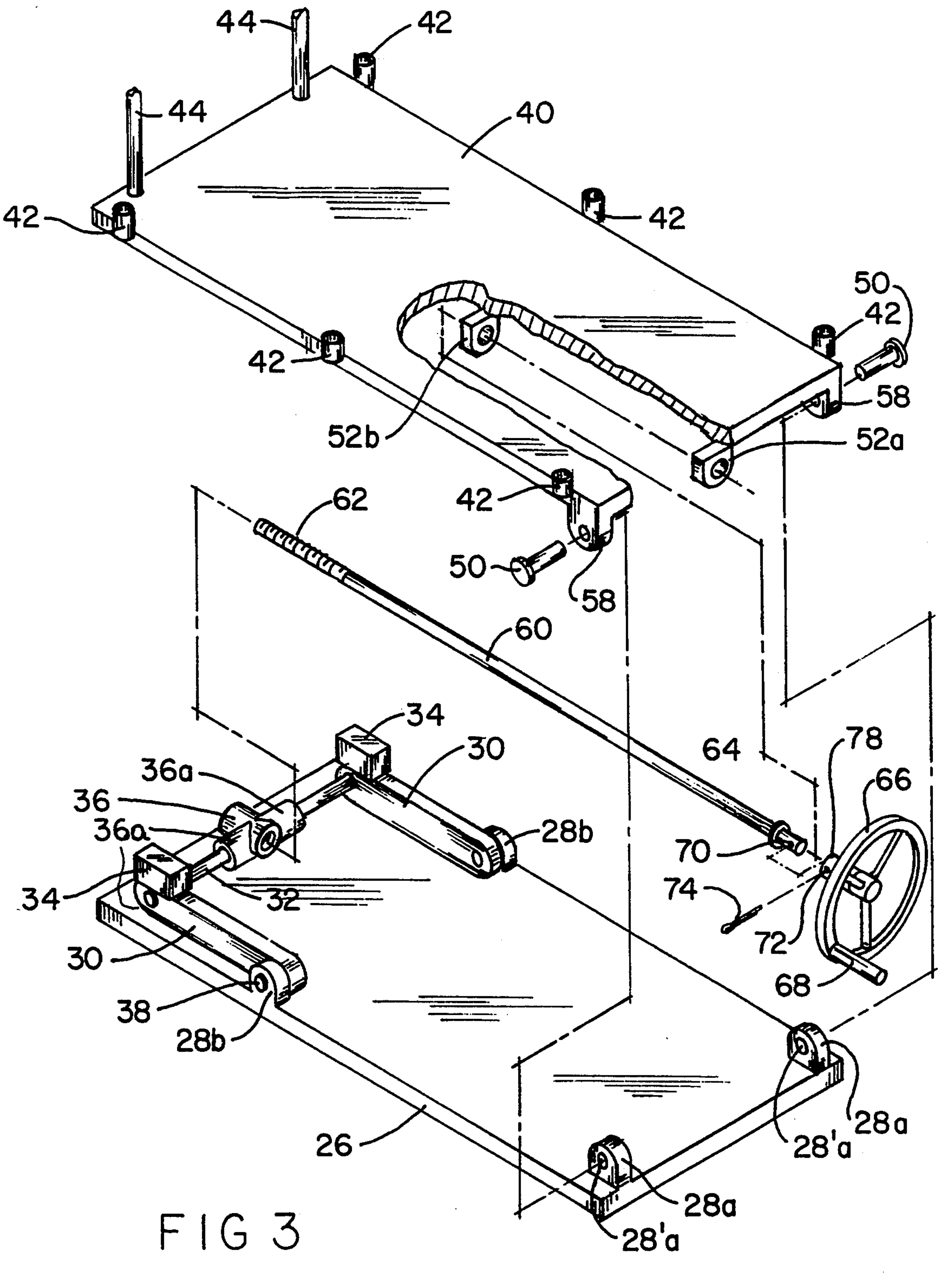
FIG. 3 is a perspective view of the separated parts used together to raise and lower the mobile traction bed of the present invention.

The modified top 26 of support structure 22 is modified as shown in FIG. 3. Extended supports 28*a* for supporting the fixed side of the base of the bed 40 have holes 28*a* which match up with holes in extended supports 58 fixed to the underside of the bed base 40. Extended supports 28*b* have holes for supporting raising arms 30. A bar 32 runs between the two raising arms 30, rotatably through a centrally positioned internally threaded raising means 36, having side sections 36*a*. Support blocks 34 for supporting the bottom of the bed base 40 at the end of the bed to be raised are themselves supported by the raising arms 30.

Support extensions 38 protrude out of the ends of raising arms 30 through holes in extended supports 28*b* to rotatably support the raising arms to the extended supports 28*b* of modified top 26, allowing for rotational movement of the support extensions 38 within the holes 28*b* as the raising arms 30 are raised and lowered.

The base of the bed 40, as also shown in FIG. 3 preferably has a plurality of fixed support rings 42. Fixed to the bottom of bed base 40 are first sleeve 52*a* for rotating bar 60 and second sleeve 52*b* for rotating bar 60. The two sleeves 52*a* and 52*b* are constructed to support rotating bar 60 which is threaded at one end 62, the threads corresponding to the internal threads of raising means 36. Support bolts 50 run through the corresponding holes in extended supports 58 in the bed base 40 and extended supports 28*a* in the support top 26 to fix the non raising side of the bed to the modified support top 26.

The rotating bar 60 can be fixed to a hand turning wheel 66 which can have a hand grip 68 for making turning easier. The hand turning wheel 66 rests against a support flange 64. A pin or key 74 can be used to fix the hand turning wheel 66 to the rotating bar 60. The key 74 goes through a key hole 72 in an extended part 78 of the wheel 66 and through a key hole 70 near the end of the rotating bar 60 and then out through a second hole (not shown and opposite hole 72) in the extended part 78 of wheel 66.

It will be appreciated that the transverse axis defined by holes 28*b* is slightly lower than the transverse axis defined by bar 32 with respect to the plane of top 26 of support structure 22 to facilitate raising of arm 32 upon rotation of hand turning wheel 66 and raising bar 60. Hence, in the bottom or rest position of arms 30 (FIG. 3), there exists an acute angle between the plane of surface 26 and a line projected in the plane of arm 30 extending between the transverse axis defined by bar 32 and the transverse axis passing through holes 28*b*. This acute angle preferably is in the range of about 10 degrees to about 15 degrees and may suitably be established by drilling the holes for bar 32 in each arm 30 slightly off-center, or placing a small fixed shim under the distal end portion of each arm 30.

Figure 4:
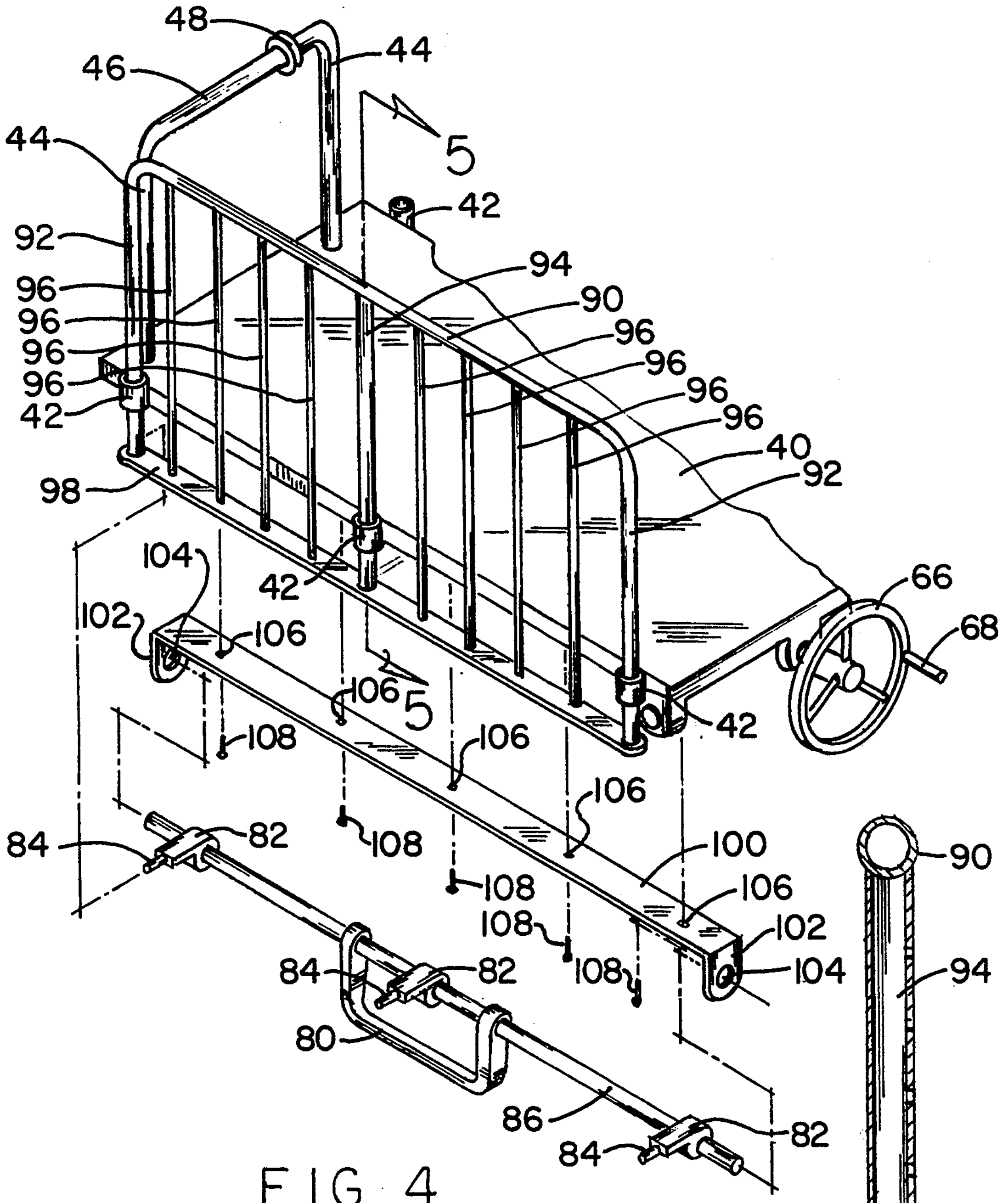
FIG. 4 is a partially separated perspective view in elevation of the railing and crossbar sections of the mobile traction bed of the present invention.
Figure 5:
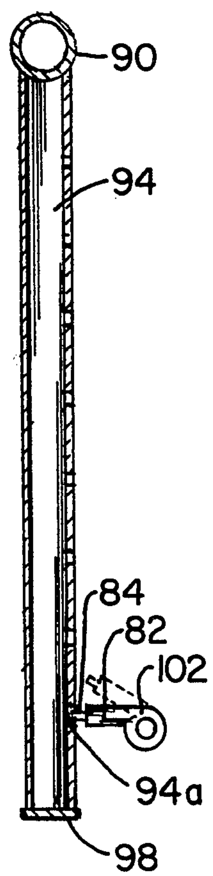
FIG. 5 is a partial cross-sectional view of the bar in the railing taken along perspective line 5—5 of FIG. 4 in accordance with the present invention.

Referring now to FIGS. 4 and 5, a traction support bar 46 having upright sections 44 is supported by the base of the bed 40. A traction weight support sleeve 48 can be fixed to the support bar 46 to provide even more support for a traction weight or pulley type system for a traction weight.

A side rail structure for the mobile traction bed of the present invention has a horizontal top section 90 of railing connected to outer vertical sections 92 of railing which run between the horizontal top section 90 and a horizontal bottom rail 98. A vertical center rail 94 (which is shown in more detail and cutaway in FIG. 5) also runs between the top horizontal rail 90 and the bottom horizontal rail 98, as do intermediate vertical rails 96, which arc preferably comprised of smaller diameter tubing. The two outer vertical rails 92 and the center vertical rail 94 have holes 94*a* near their bottom (see the center rail 94 as shown in FIG. 5).

A handle 80 is fixed to a rotatable pin holding bar 86 having pin holding extensions 82 with pins 84 extending therefrom. These pins 84 correspond with the holes 94*a* described above. The rotatable pin holding bar 86 is held in position by flat supporting rail 100 which is fixed to the bottom of the base of the bed 40 preferably with screws 108 passing through the holes 106 and into the bottom of the base of the bed 40. The ends of bar 86 are held in holes 104 in the downturned ends 102 of flat support rail 100. The bar 86 can be rotated so that the pins 84 can enter the holes 94*a* of the vertical rails 92 and 94 as shown in FIG. 5. By rotating the bar 86 by means of handle 80 the pins 84 can be engaged and disengaged with the holes 94*a* to either support the rails or allow them to drop down.

The mobile traction bed of the present invention is very simple to operate. The bed can be taken out of its storage position as shown in FIG. 1 and the vertical support bars 22*a* can be fully extended as they are shown in FIG. 2. The handle 80 (refer to FIG. 4) can be turned to disengage pins 84 from the holes 94*a* in the vertical bars 92 and 94 allowing the side rail to slide down, the outer vertical bars 92 and the center vertical bar 94 sliding through support rings 42. The patient can be put onto the base of the bed 40 (or a comfortable mattress covering the base) and then the side rail structure can be slid back up and the handle 80 turned back to engage the pins 84 with the holes 94*a* to hold the side rail structure up safely, securing the patient in the bed.

Once the side rail structure is secured, the end of the bed can be raised by turning the raising wheel 66 using the handle 68. The turning motion causes the bar 60 to rotate which in turn causes the threaded end section 62 of the bar 60 to rotate. The rotating threads engage with the internally threaded means 36, which, as the wheel 66 is turned, slowly pulls the internally threaded means 36 closer toward the wheel 66 along the threaded bar 60. As the internally threaded means 36 moves along the bar 60, the arms 30 raise upward, pivoting at the upward extensions 28*b*. As the arms 30 raise upward, they force the support blocks 34 upward, the support blocks 34 pushing the end of the base of the bed 40 upward. The bed can be raised until that part of the patient's body which is to be held in traction is at a higher elevation than the patient's heart.

The traction weight can then be allowed to hang by a cable or other hanging means from the traction weight support bar 46, preferably using sleeve 48 to keep the hanging means from sliding around out of control.

The raised bed can be lowered when necessary by turning the wheel 66 in the opposite direction.

It is apparent from the above that the present invention accomplishes all of the objectives set forth by providing a new and improved traction bed which can be moved from one location to another without harm or discomfort to the patient having a device for raising the bed to an angle such that the part of the body to be held in traction can be kept above the heart's level. The mobile traction bed also has a unique opening and closing side rail for keeping the patient safe and secure within the bed. The traction side of the bed can have a bar and sleeve for supporting traction weights. By using the mobile traction bed, the patient can rest at home instead of at the hospital, yet can be moved to and from the hospital as is required.

With respect to the above description, it should be realized that the optimum dimensional relationships for the parts of the invention, to include variations in size, materials, shape, form, function and manner of operation, assembly and use, are deemed readily apparent and obvious to those skilled in the art. Therefore, all relationships equivalent to those illustrated in the drawings and described in the specification are intended to be encompassed only by the scope of appended claims.

The present invention mobile traction bed can be used for children and adults. The invention can be transported to and from the hospital in a standard ambulance. The mobile traction bed can be made to meet all of the legal requirements of a stretcher. The device allows a patient to come home from the hospital much sooner previously possible. The device can be easily adapted to work with a variety of different types of bone fractures and the like. The patient can be transported to and from the hospital in the mobile traction bed when X-rays and further check ups are necessary.

The mobile traction bed of the present invention will save great amounts of money to users since they will no longer require long, expensive hospital stays.

Removable extras can be added to the bed so that patients can entertain themselves. For example, attachable chalkboards, tables, cup holders, bells and the like can be added.

While the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed as being new and desired to be protected by Letters Patent of the United States is as follows:

1. A mobile traction bed comprising:

a plurality of wheel supports;

a plurality of wheels, with each of said wheels being rotatably mounted to an individual one of said wheel supports;

a first horizontal support bar extending between a first and a second of said wheel supports, and a second horizontal support bar extending between a third and a fourth of said wheel supports;

a plurality of central flex joints;

a plurality of vertical support posts, said vertical support posts being pivotally joined in pairs by said central flex joints, with each of said pairs of vertical support posts being mounted to and projecting upwardly from an individual one of said wheel supports, said central flex joints permitting said pairs of vertical support posts to be folded upon each other;

a modified top having a substantially rectangular shape defining four corners thereof, said modified top being mounted at said corners thereof to said pairs of support posts, said modified top having opposed sides and first and second ends;

a pair of raising arms pivotally mounted to said modified top at said opposed sides thereof, said raising arms each having a distal end with a bar extending between said distal ends of said raising arms;

a bed having first and second ends, said bed being pivotally mounted at said first end thereof to said first end of said modified top, said bed having a first sleeve mounted to and depending downwardly from said first end of said bed;

a rotating bar rotatably supported by said first sleeve and threadably engaged to a portion of said bar such that a rotation of said rotating bar will cause a pivoting of said raising arms relative to said modified top, said raising arms each having a support block which engages said bed to effect a pivoting of said bed about said first end of said bed during pivoting of said raising arms relative to said modified top;

a side rail structure slidably mounted to said bed, said side rail structure including a horizontal top section having a center and first and second ends, with outer vertical sections connected to and depending downwardly from said ends of said horizontal top section, a center rail connected to and extending downwardly from said center of said horizontal top section, and a plurality of intermediate vertical rails connected to and extending downwardly from said horizontal top section, with said outer vertical sections and said center rail having a plurality of longitudinally spaced holes;

a flat supporting rail mounted to said bed;

a rotatable pin holding bar having pins extending therefrom, said pin holding bar being pivotally mounted to said supporting rail, said pins being rotatably positionable within said longitudinally spaced holes so as to secure said side rail structure relative to said bed; and, a handle fixedly secured to said pin holding bar for facilitating a rotation of said pin holding bar such that as said side rail structure is being lowered relative to said bed, said handle can be pivoted by a user to rotatably position said pins into said longitudinally spaced holes during said lowering of said side rail structure.

* * * * *